United States Patent [19]

Mentrup et al.

[11] 4,046,913

[45] Sept. 6, 1977

[54] 1-(M-ALKANOYLOXY-PHENYL)-1-HYDROXY-2-(N-LOWER ALKYL-AMINO)-ETHANES AND SALTS THEREOF

[75] Inventors: Anton Mentrup; Kurt Schromm; Ernst-Otto Renth, all of Ingelheim am Rhein; Werner Traunecker, Munster-Sarmsheim, all of Germany

[73] Assignee: Boehringer Ingelheim GmbH, Ingelheim am Rhein, Germany

[21] Appl. No.: 660,401

[22] Filed: Feb. 23, 1976

Related U.S. Application Data

[63] Continuation-in-part of Ser. No. 497,726, Aug. 15, 1974, abandoned.

[30] Foreign Application Priority Data

Aug. 18, 1973 Germany .............................. 2341876

[51] Int. Cl.² .................... A61K 31/22; C07C 67/08
[52] U.S. Cl. ..................................... 424/311; 560/142
[58] Field of Search ..................... 424/311; 260/479 R

[56] References Cited

U.S. PATENT DOCUMENTS

| 3,180,887 | 4/1965 | Zolss et al. ................... 260/479 R |
| 3,463,808 | 4/1969 | Bond et al. ................... 260/479 R |
| 3,642,896 | 2/1972 | Collin ........................... 260/479 R |
| 3,657,244 | 4/1972 | Mentrup et al. ..................... 424/311 |
| 3,726,919 | 4/1973 | Wooldridge et al. ........... 260/479 R |
| 3,825,583 | 7/1974 | Hussain et al. ................. 260/479 R |
| 3,868,461 | 2/1975 | Hussain et al. ...................... 424/311 |

FOREIGN PATENT DOCUMENTS

| 2,152,058 | 4/1973  | Germany ............................. 424/311 |
| 1,298,771 | 12/1972 | United Kingdom |
| 1,298,772 | 12/1972 | United Kingdom |

*Primary Examiner*—Norman A. Drezin
*Attorney, Agent, or Firm*—Hammond & Littell

[57] ABSTRACT

Compounds of the formula

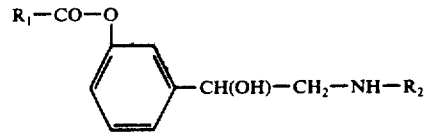

wherein
$R_1$ is alkyl of 6 to 19 carbon atoms, and
$R_2$ is methyl or ethyl, and their non-toxic, pharmacologically acceptable acid addition salts; the compounds as well as the salts are useful as pharmaceuticals for the treatment of cardiac and circulatory insufficiencies.

3 Claims, No Drawings

1-(M-ALKANOYLOXY-PHENYL)-1-HYDROXY-2-(N-LOWER ALKYL-AMINO)-ETHANES AND SALTS THEREOF

This is a continuation-in-part of copending application Ser. No. 497,726 filed Aug. 15, 1974, now abandoned.

The present invention relates to novel 1-(m-alkanoyloxy-phenyl)-1-hydroxy-2-(N-lower alkyl-amino)-ethanes and non-toxic acid addition salts thereof, as well as to a method of preparing these compounds.

More particularly, the present invention relates to a novel class of 1-(m-alkanoyloxy-phenyl)-1-hydroxy-2-(N-lower alkyl-amino)-ethanes represented by the formula

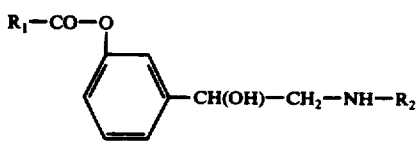

(I)

wherein $R_1$ is alkyl of 6 to 19 carbon atoms, and
$R_2$ is methyl or ethyl, and their non-toxic, pharmacologically acceptable acid addition salts.

The compounds of the formula I comprise an asymmetric carbon atom and may therefore occur in the form of racemates as well as in the form of optically active compounds.

The compounds embraced by formula I are prepared by reduction of a corresponding acetophenone derivative of the formula

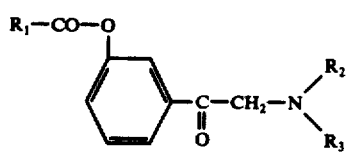

(II)

wherein $R_1$ and $R_2$ have the meanings defined above, and $R_3$ is hydrogen or optionally substituted benzyl. The benzyl group may be substituted, for example, by alkyl or alkoxy groups or halogen. The reduction is effected by catalytic hydrogenation with conventional hydrogenation catalysts, such as palladium, platinum or nickel, or with complex metal hydrides of lower reducing power, such as sodium borohydride.

When $R_3$ in formula II is a benzyl group, it is simultaneously removed during the catalytic hydrogenation. If the reduction of the keto group is effected with a complex metal hydride, the benzyl group is subsequently removed by catalytic hydrogenation.

The starting compounds of the formula II may be obtained by acylation of a m-hydroxy-acetophenone of the formula

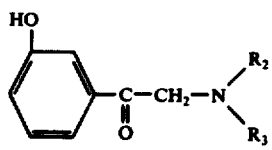

(III)

wherein $R_2$ and $R_3$ have the meanings defined above, with an acid chloride of the formula

$R_1 - CO - Cl$ (IV)

wherein $R_1$ has the meanings previously defined, optionally followed by removal of the benzyl group by selective hydrogenation.

If the above-described process yields a racemate of a compound of the formula I, the same may, if desired, be separated into its optical antipode components by conventional methods.

The compounds embraced by formula I are organic bases and therefore form acid addition salts with inorganic or organic acids. Examples of non-toxic, pharmacologically acceptable acid addition salts are those formed with such as hydrochloric acid, hydrobromic acid, hydroiodic acid, hydrofluoric acid, sulfuric acid, phosphoric acid, nitric acid, acetic acid, propionic acid, butyric acid, caproic acid, capric acid, valeric acid, oxalic acid, malonic acid, succinin acid, maleic acid, fumaric acid, lactic acid, tartaric acid, citric acid, benzoic acid, p-hydroxybenzoic acid, p-aminobenzoic acid, phthalic acid, cinnamic acid, salicylic acid, ascorbic acid, methanesulfonic acid, ethanephosphonic acid, 8-chlorotheophyllin, or the like.

The following examples illustrate the present invention and will enable others skilled in the art to understand it more completely. It should be understood, however, that the invention is not limited solely to the particular examples given below.

EXAMPLE 1

1-(m-Stearyloxy-phenyl)-1-hydroxy-2-(N-ethylamino)-ethane hydrochloride a. m-Stearyloxy-ω-(N-ethylamino)-acetophenone hydrochloride 94.5 gm (0.312 mol) of stearoyl chloride were added dropwise to a solution of 53.8 gm (0.25 mol) of m-hydroxy-ω-(N-ethylamino)-acetophenone hydrochloride in 100 ml of trifluoroacetic acid at 30° C, accompanied by stirring. The resulting reaction mixture was stirred for five minutes at 60° C and was then without cooling it, stirred into 1 liter of ethyl acetate. A crystalline precipitate was formed thereby which was collected by vacuum filtration, washed with ethyl acetate and recrystallized from ethanol, yielding 108 gm (89.6% of theory) of m-stearyloxy-ω-(N-ethylamino)-acetophenone hydrochloride having a melting point of 195° C.

b. 72 gm (0.15 mol) of the product obtained in step (a) were hydrogenated in 1.44 liters of methanol and in the presence of 5 gm of 5% palladium charcoal at 5 atmospheres and 60° C. After the absorption of hydrogen had ceased, the catalyst was filtered off, and the methanol was distilled out of the filtrate. The crystalline residue was stirred with acetonitrile, the mixture was vacuum-filtered, and the filter cake was recrystallized from ethanol, yielding 69 gm (95.% of theory) of the compound of the formula

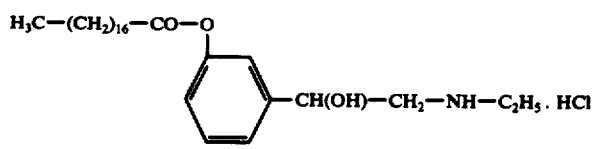

which had a melting point of 113° C.

EXAMPLE 2

Using a procedure analogous to that described in Example 1, 86.4% of theory of 1-(m-heptanoyloxy-phenyl)-1-hydroxy-2-(N-ethylamino)-ethane hydrochloride, m.p. 120° C (recrystallized from ethyl acetate), was obtained from m-heptanoyloxy-ω-(N-ethylamino)-acetophenone hydrochloride.

EXAMPLE 3

Using a procedure analogous to that described in Example 1, 89.2% of theory of 1-(m-hexadecanoyloxy-phenyl)-1-hydroxy-2-(N-ethylamino)-ethane hydrochloride, m.p. 115° C (recrystallized from ethanol), was obtained from m-hexadecanoyloxy-ω-(N-ethylamino)-acetophenone hydrochloride.

EXAMPLE 4

Using a procedure analogous to that described in Example 1, 96.5% of theory of 1-(m-stearyloxy-phenyl)-1-hydroxy-2-(N-methylamino)-ethane hydrochloride, m.p. 96° C (recrystallized from ethanol), was obtained from m-stearoyloxy-ω-(N-ethylamino)-acetophenone hydrochloride.

The compounds of the present invention, that is, those embraced by formula I and their non-toxic, pharmacologically acceptable acid addition salts, have useful pharmacodynamic properties; more particularly, they enhance the circulation and the function of the heart and are therefore effective for the treatment of cardiac and circulatory insufficiency in warm-blooded animals, such as cats.

For pharmaceutical purposes the compounds according to the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.083 to 1.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless other specified.

EXAMPLE 5

Tablets

The tablet composition is compounded from the following ingredients:

| | |
|---|---|
| 1-(m-Stearyloxy-phenyl)-1-hydroxy-2-(N-ethylamino)-ethane hydrochloride | 5 parts |
| Stearic acid | 6 parts |
| Dextrose | 589 parts |
| Total | 600 parts |

Preparation

The ingredients are compounded in conventional manner, and the composition is compressed into 600 mgm-tablets. Each tablet contains 5 mgm of the active ingredient and is an oral dosage unit composition effective for the treatment of cardiac and circulatory insufficiency.

EXAMPLE 6

Suppositories

The suppository composition is compounded from the following ingredients:

| | |
|---|---|
| 1-(m-Heptanoyloxy-phenyl)-1-hydroxy-2-(N-ethylamino)-ethane hydrochloride | 5 parts |
| Lactose, powdered | 45 parts |
| Suppository base (e.g. cocoa butter) | 1650 parts |
| Total | 1700 parts |

Preparation

The active ingredient and the lactose are intimately admixed with each other, the mixture is homogeneously blended into the melted suppository base, and 1700 mgm-portions of the resulting composition are poured into cooled suppository molds and allowed to harden therein. Each suppository contains 5 mgm of the active ingredient and is a rectal dosage unit composition effective for the treatment of cardiac and circulatory insufficiency.

Analogous results are obtained when any one of the other compounds embraced by formula I or a non-toxic, pharmacologically acceptable acid addition salt thereof is substituted for the particular active ingredient in Examples 5 and 6. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 1-(m-Stearyloxy-phenyl)-1-hydroxy-2-(N-ethylamino)-ethane or a non-toxic, pharmacologically acceptable acid addition salt thereof.

2. A pharmaceutical dosage unit composition consisting essentially of an inert pharmaceutical carrier and an effective circulation and heart function enhancing amount of a compound of claim 1.

3. The method of treating cardiac and circulatory insufficiency in a warm-blooded animal in need thereof, which comprises administering to said animal an effective circulation and heart function enhancing amount of a compound of claim 1.

* * * * *